(12) United States Patent  
Minh

(10) Patent No.: US 7,888,933 B2
(45) Date of Patent: Feb. 15, 2011

(54) METHOD FOR ESTIMATING FORMATION HYDROCARBON SATURATION USING NUCLEAR MAGNETIC RESONANCE MEASUREMENTS

(75) Inventor: Chanh Cao Minh, Katy, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 186 days.

(21) Appl. No.: 12/364,104

(22) Filed: Feb. 2, 2009

(65) Prior Publication Data

US 2009/0206834 A1 Aug. 20, 2009

Related U.S. Application Data

(60) Provisional application No. 61/028,957, filed on Feb. 15, 2008.

(51) Int. Cl.
*G01V 3/00* (2006.01)
(52) U.S. Cl. ........................ 324/303; 324/300
(58) Field of Classification Search ........... 324/300, 324/303; 702/7, 13; 73/152.05, 152.06
See application file for complete search history.

(56) References Cited

U.S. PATENT DOCUMENTS

| 6,808,028 | B2 * | 10/2004 | Woodburn et al. ............. 175/48 |
| 6,936,812 | B2 * | 8/2005 | Odom et al. ............. 250/269.5 |
| 7,157,915 | B2 * | 1/2007 | Schoen et al. ............... 324/339 |
| 7,617,050 | B2 * | 11/2009 | Allen et al. ..................... 702/7 |
| 2007/0143021 | A1 * | 6/2007 | Griffiths et al. ................ 702/6 |
| 2009/0043510 | A1 * | 2/2009 | Allen et al. ................... 702/13 |
| 2010/0026293 | A1 * | 2/2010 | Minh ......................... 324/303 |
| 2010/0109664 | A1 * | 5/2010 | Minh ......................... 324/303 |

* cited by examiner

*Primary Examiner*—Brij B Shrivastav
(74) *Attorney, Agent, or Firm*—Shaun B. Sethna; Darla Fonseca; Charlotte Rutherford

(57) ABSTRACT

A method for estimating fluid saturation in a formation penetrated by a wellbore from nuclear magnetic resonance measurements made at a plurality of lateral depths into the formation from the wellbore includes estimating a bound water volume, a total porosity and a free water volume at each of the lateral depths from the nuclear magnetic resonance measurements. A minimum water saturation is estimated at each lateral depth from the total porosity, the free water volume and the bound water volume at each lateral depth. A value of water saturation is estimated at each lateral depth from the minimum water saturation at each lateral depth. A relationship between lateral depth and water saturation is determined. Water saturation is estimated at a selected lateral depth greater than the greatest lateral depth of the nuclear magnetic resonance measurements.

10 Claims, 3 Drawing Sheets

US 7,888,933 B2

METHOD FOR ESTIMATING FORMATION HYDROCARBON SATURATION USING NUCLEAR MAGNETIC RESONANCE MEASUREMENTS

CROSS-REFERENCE TO RELATED APPLICATIONS

Priority is claimed from U.S. Provisional Application No. 61/028,957 filed on Feb. 15, 2008.

STATEMENT REGARDING FEDERALLY SPONSORED RESEARCH OR DEVELOPMENT

Not applicable.

BACKGROUND OF THE INVENTION

1. Field of the Invention

The invention relates generally to the field of well log interpretation. More specifically, the invention relates to methods for determining hydrocarbon saturation in the pore spaces of subsurface rock formations at lateral distances ("depths of investigation") greater than that of measurements made by well logging instruments that probe near-wellbore regions such as—but not limited—to nuclear magnetic resonance.

2. Background Art

Nuclear magnetic resonance ("NMR") well logging instruments known in the art make measurements related to certain nuclear magnetization properties of subsurface fluids in the rock formations. Such properties include longitudinal and transverse relaxation times of the various fluids in the formations, and diffusion constants of such fluids. The measurements may be used for determining the fractional volume of pore space in porous formations that is filled with water (called "water saturation" and represented by Sw). Such water saturation determinations may be made independently of other water saturation related parameters, e.g., the electrical resistivity of the formations using. NMR water saturation determinations may be made, for example, diffusion-relaxation maps. As is known in the art, the fractional volume of pore space in a subsurface rock formation that is not occupied by connate water or the liquid phase of drilling fluid is generally assumed to be filled with connate hydrocarbons, including oil, gas and mixtures thereof. Such hydrocarbon content is used for, among other purposes, evaluating the probable fluid production properties of subsurface rock formations.

NMR measurements are particularly useful in subsurface formations that have large uncertainties about parameters used in determining Sw from electrical resistivity measurements (so-called "Archie" determination) such as unknown connate water resistivity (resistivity of naturally occurring water disposed in the formation pore spaces), complex pore geometry, unknown cementation factor m, unknown wettability (n), high clay content (particularly where there is high clay electrical conductivity relative to water electrical conductivity), among other factors. However, NMR well logging instruments known in the art typically measure properties of the subsurface rock formations at relatively shallow depths of investigation into the formations. Depth of investigation is used to mean the lateral distance into the rock formation from the wall of the wellbore in which the NMR instrument is disposed for measurement. At shallow depths of investigation (close to the wellbore wall), the water saturation may not be representative of the natural (undisturbed) water saturation in the formations because of infiltration of liquid phase of drilling fluid into the pore spaces proximate the wellbore. The foregoing is particularly problematic when "oil based" drilling fluids (those in which hydrocarbon is the continuous liquid phase) are used to drill through subsurface rock formations. When such oil based drilling fluids are used, the liquid phase of the drilling fluid that infiltrates the formation pore spaces is primarily oil or other liquid hydrocarbon, and such hydrocarbon may displace connate hydrocarbons, connate water, or mixtures thereof.

There is a need for techniques to use NMR well logging measurements to better estimate natural or undisturbed water saturation in subsurface rock formations.

SUMMARY OF THE INVENTION

One aspect of the invention is a method for estimating fluid saturation in a formation penetrated by a wellbore from nuclear magnetic resonance measurements made at a plurality of lateral depths into the formation from the wellbore. A method according to this aspect of the invention includes estimating a bound water volume, a total porosity and a free water volume at each of the lateral depths from the nuclear magnetic resonance measurements. A minimum water saturation is estimated at each lateral depth from the total porosity, the free water volume and the bound water volume at each lateral depth. A value of water saturation is estimated at each lateral depth from the minimum water saturation at each lateral depth. A relationship between lateral depth and water saturation is determined. Water saturation is estimated at a selected lateral depth greater than the greatest lateral depth of the nuclear magnetic resonance measurements.

A method for well logging according to another aspect of the invention includes moving a nuclear magnetic resonance instrument along a wellbore drilled through subsurface rock formations. Nuclear magnetic resonance properties are measured at a plurality of lateral depths into the formations from a wall of the wellbore. Corresponding to at least one axial position along the wellbore, a bound water volume, a total porosity and a free water volume are estimated at each of the lateral depths from the nuclear magnetic resonance measurements. A minimum water saturation is estimated at each lateral depth from the total porosity, the free water volume and the bound water volume at each lateral depth. A value of water saturation is estimated at each lateral depth from the minimum water saturation at each lateral depth. A relationship between lateral depth and water saturation is determined. Water saturation is estimated at a selected lateral depth greater than the greatest lateral depth of the nuclear magnetic resonance measurements.

Other aspects and advantages of the invention will be apparent from the following description and the appended claims.

DETAILED DESCRIPTION

Figure 1A:
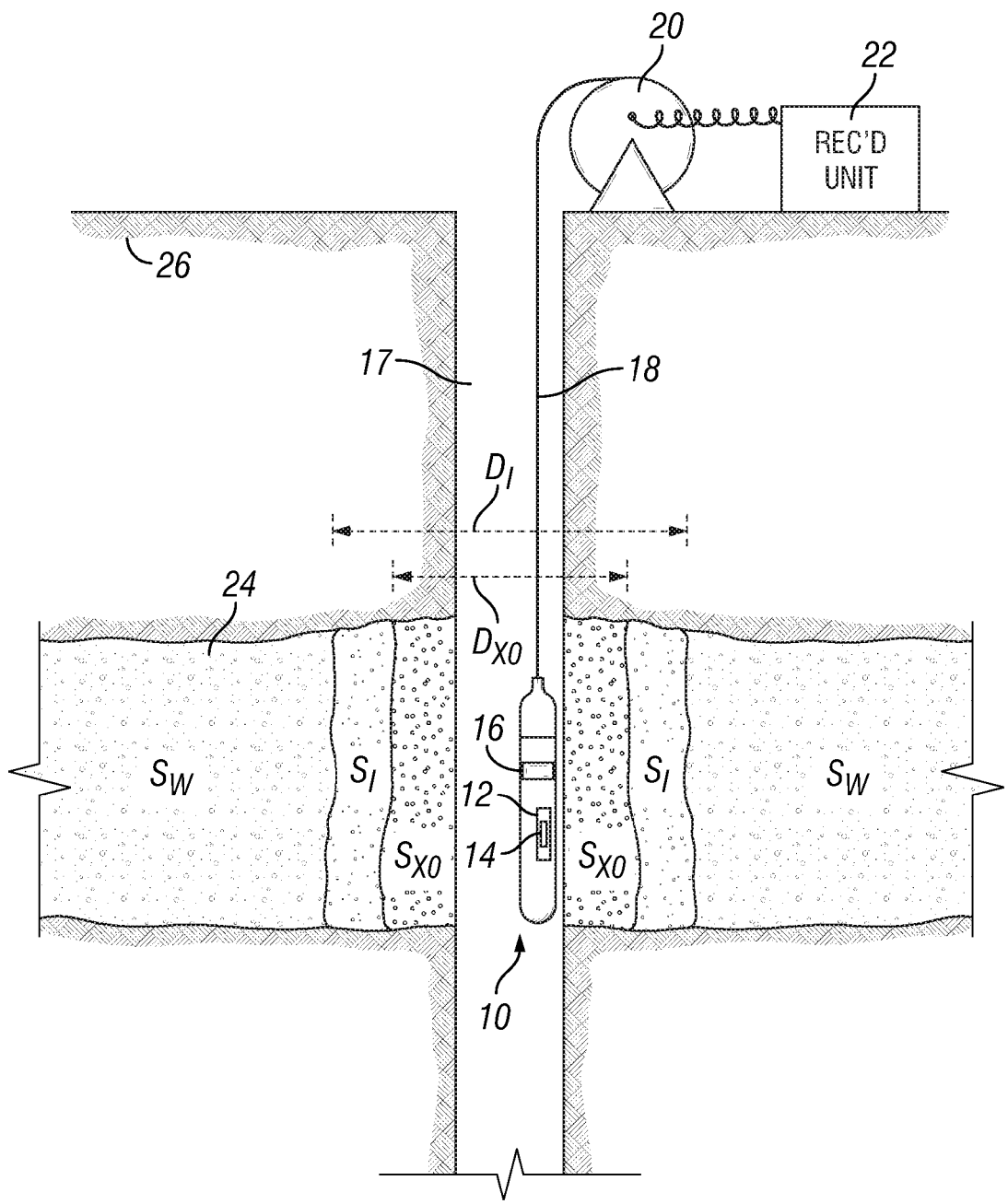
FIG. 1A shows a wireline NMR instrument deployed in a wellbore.

FIG. 1A shows an example nuclear magnetic resonance ("NMR") wireline well logging instrument 10 disposed in a wellbore 17 drilled through subsurface rock formations 26, 24. The instrument 10 is disposed at one end of an armored electrical cable ("wireline") 18. The cable 18 may be extended into the wellbore 17 and withdrawn by a spooling device such as a winch 20 of types well known in the art. The cable 18 includes one or more electrical and/or optical conductors to communicate signals between the instrument 10 and a recording unit 22 disposed at the surface. The recording unit 22 may include a computer (not shown separately) having a screen or printer type data display and a data recording device for storage of signals (e.g., NMR measurements) communicated from the well logging instrument as well as calculated results made from the NMR measurements.

The NMR instrument 10 includes a magnet 12 for inducing a static magnetic field in the formations 24, 26 as the instrument 10 is moved along the interior of the wellbore 17. The instrument 10 also includes an antenna for inducing radio frequency ("RF") magnetic fields in the formations, and for detecting radio frequency signals induced by NMR phenomena excited in the formations by the static and RF magnetic fields. The particular portion of the formations adjacent to the wellbore from which the NMR signals originate depends on, among other factors, the spatial amplitude distribution of the static magnetic field and the RF frequency used to induce NMR phenomena in the formations.

A particular formation of interest is illustrated at 24 in FIG. 1A to explain the invention. Proximate the wall of the wellbore 17, a portion of the formation 24 may be subjected to sufficient infiltration of the liquid phase of a fluid ("drilling mud"), called "mud filtrate", used to drill the wellbore 17, that substantially all of the mobile connate fluids in the pore spaces of the formation 24 are displaced by the mud filtrate. Depending on, for example, the fractional volume of pore space ("porosity") of the formation 24, and the filtrate characteristics of the drilling mud, the mud filtrate will fully displace all the mobile connate fluids to a depth represented by $d_{xo}$ in FIG. 1A. The foregoing is referred to as the diameter of the "flushed zone." Partial displacement of connate fluid is shown extending to a diameter represented by $d_i$, which is used to represent the diameter of the "invaded zone." At a certain lateral depth in the formation 24, beyond the diameter of the invaded zone, connate fluid is substantially undisturbed. As explained in the Background section herein, a quantity of interest in determining possible fluid production in from the formation is the factional volume of the pore space that is occupied by water (and its complement assumed to be occupied by hydrocarbons). In the uninvaded zone, such fractional volume, called "saturation" as explained in the Background section herein, is represented by Sw. Invaded zone and flushed zone water saturations are represented, respectively, by Si and Sxo.

The example instrument shown in FIG. 1A is only for purposes of explaining the source of measurements that may be used with a method according to the invention and is not intended to limit the configurations of NMR well logging instrument that may be used to provide measurements for the method of the present invention.

Figure 1B:
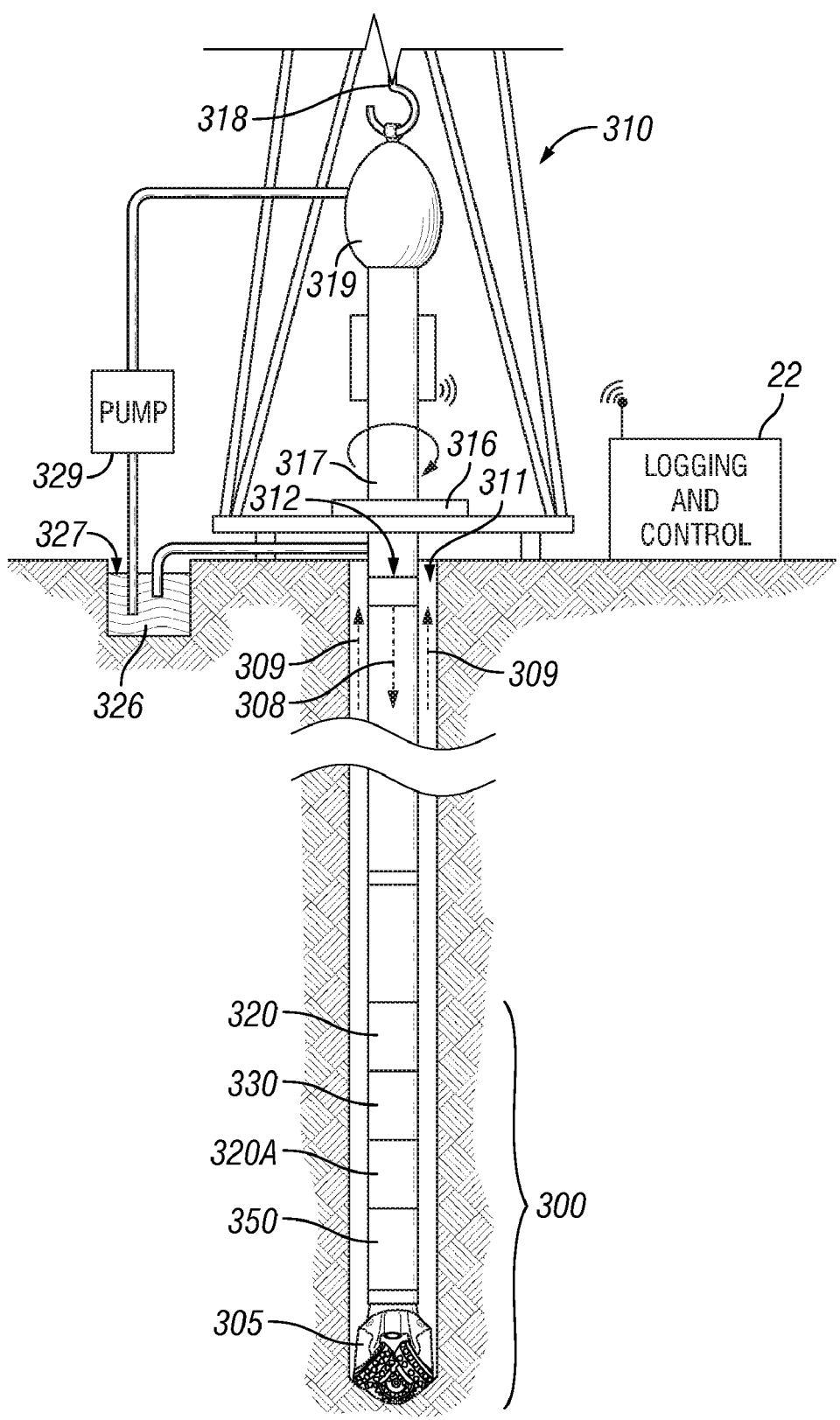
FIG. 1B shows a logging while drilling NMR instrument deployed in a wellbore.

FIG. 1B illustrates a wellsite system in which an NMR well logging instrument can be conveyed using a drill string for measurement during the drilling of the wellbore, or during other drill string operations associated with the construction of a wellbore such as circulating and "tripping." The wellsite can be onshore or offshore. In the example system of FIG. 1B, a wellbore 311 is drilled through subsurface formations by rotary drilling in a manner that is well known in the art. Other example of the invention can be used in connection with directional drilling apparatus and methods, as will be described hereinafter.

A drill string 312 is suspended within the wellbore 311 and includes a bottom hole assembly ("BHA") 300 proximate the lower end thereof. The BHA 300 includes a drill bit 305 at its lower end. The surface portion of the wellsite system includes a platform and derrick assembly 310 positioned over the wellbore 311, the assembly 310 including a rotary table 316, kelly 317, hook 318 and rotary swivel 319. The drill string 312 is rotated by the rotary table 316, which is itself operated by well known means not shown in the drawing. The rotary table 316 engages the kelly 317 at the upper end of the drill string 312. The drill string 312 is suspended from the hook 318. The hook 318 is attached to a traveling block (also not shown), through the kelly 317 and the rotary swivel 319 which permits rotation of the drill string 312 relative to the hook 318. As is well known, a top drive system (not shown) could alternatively be used instead of the kelly 317 and rotary table 316 to rotate the drill string 312 from the surface.

In the present example, the surface system further includes drilling fluid ("mud") 326 stored in a tank or pit 327 formed at the wellsite. A pump 329 delivers the drilling fluid 326 to the interior of the drill string 312 via a port in the swivel 319, causing the drilling fluid 326 to flow downwardly through the drill string 312 as indicated by the directional arrow 308. The drilling fluid 326 exits the drill string 312 via water courses, or nozzles ("jets") in the drill bit 305, and then circulates upwardly through the annulus region between the outside of the drill string and the wall of the borehole, as indicated by the directional arrows 309. In this well known manner, the drilling fluid 326 lubricates the drill bit 305 and carries formation cuttings up to the surface, whereupon the drilling fluid 326 is cleaned and returned to the pit 327 for recirculation.

The bottom hole assembly 300 of the illustrated example can include a logging-while-drilling (LWD) module 320, a measuring-while-drilling (MWD) module 330, a steerable directional drilling system such as a rotary steerable system and/or an hydraulically operated motor such as a steerable motor, and the drill bit 305.

The LWD module 320 is housed in a special type of drill collar, as is known in the art, and can contain one or a plurality of known types of well logging instruments. It will also be understood that more than one LWD and/or MWD module can be used, e.g. as represented at 320A. (References, throughout, to a module at the position of LWD module 320 can alternatively mean a module at the position of MWD module 320A as well.) The LWD module 320A typically includes capabilities for measuring, processing, and storing information, as well as for communicating with the surface equipment. In the present embodiment, the LWD module 320 includes an NMR measuring instrument. An example configuration of such instrument is explained above with reference to FIG. 1A.

The MWD module 330 is also housed in a special type of drill collar, as is known in the art, and can contain one or more devices for measuring characteristics of the drill string and drill bit. The MWD module 330 further includes an apparatus (not shown) for generating electrical power for the downhole portion of the wellsite system. Such apparatus typically includes a turbine generator powered by the flow of the drilling fluid 326, it being understood that other power and/or battery systems may be used while remaining within the scope of the present invention. In the present example, the MWD 330 module can include one or more of the following types of measuring devices: a weight-on-bit measuring device, a torque measuring device, a vibration measuring device, a shock measuring device, a stick slip measuring device, a direction measuring device, and an inclination measuring device.

The foregoing examples of wireline and drill string conveyance of a well logging instrument are not to be construed as a limitation on the types of conveyance that may be used for the well logging instrument. Any other conveyance known in the art may be used, including without limitation, slickline (solid wire cable), coiled tubing, well tractor and production tubing.

A recording unit 22 may be disposed at the surface and may include data acquisition, recording and display devices similar to those of the recording unit shown at 22 in FIG. 1A.

In an example method according to the invention, measurements of nuclear magnetic resonance ("NMR") properties of subsurface formations may be made at a plurality of lateral depths into the formations adjacent to the wellbore. A NMR instrument, as explained above with reference to FIGS. 1A and 1B, can be moved along a wellbore drilled through subsurface formations. As explained with reference to FIG. 1A, NMR measurement made by the instrument includes prepolarizing nuclei in the formations by imparting a static magnetic field in the formations. The static magnetic field has known spatial amplitude distribution and known spatial gradient distribution. NMR phenomena are excited in the formations by applying a radio frequency ("RF") magnetic field to the prepolarized nuclei. A frequency of the RF magnetic field is selected to excite NMR phenomena in selected types of nuclei and within particular volumes in the formations ("sensitive volumes"). As is known in the art, the spatial position of the sensitive volumes depends on the spatial distribution of the amplitude of the static magnetic field, the gyromagnetic ratio of the selected nuclei and the frequency of the RF magnetic field. Electromagnetic fields resulting from the induced NMR phenomena are detected and analyzed to determine NMR properties of the formations within the sensitive volumes. Such properties may include distribution of longitudinal and transverse relaxation times ($T_1$ and $T_2$, respectively) and diffusion constants (D) of the various components of the formations. The foregoing parameters may be used to estimate, as non limiting examples, the total fractional volume of pore space ("total porosity") of the various subsurface formations, the bulk volume of "bound" water (water that is chemically or otherwise bound to the formation rock grains, such as by capillary pressure, and is therefore immobile), the fractional volume of the pore space occupied by movable water ("free water") and the fractional volume of the pore space occupied by oil and/or gas.

Figure 2:
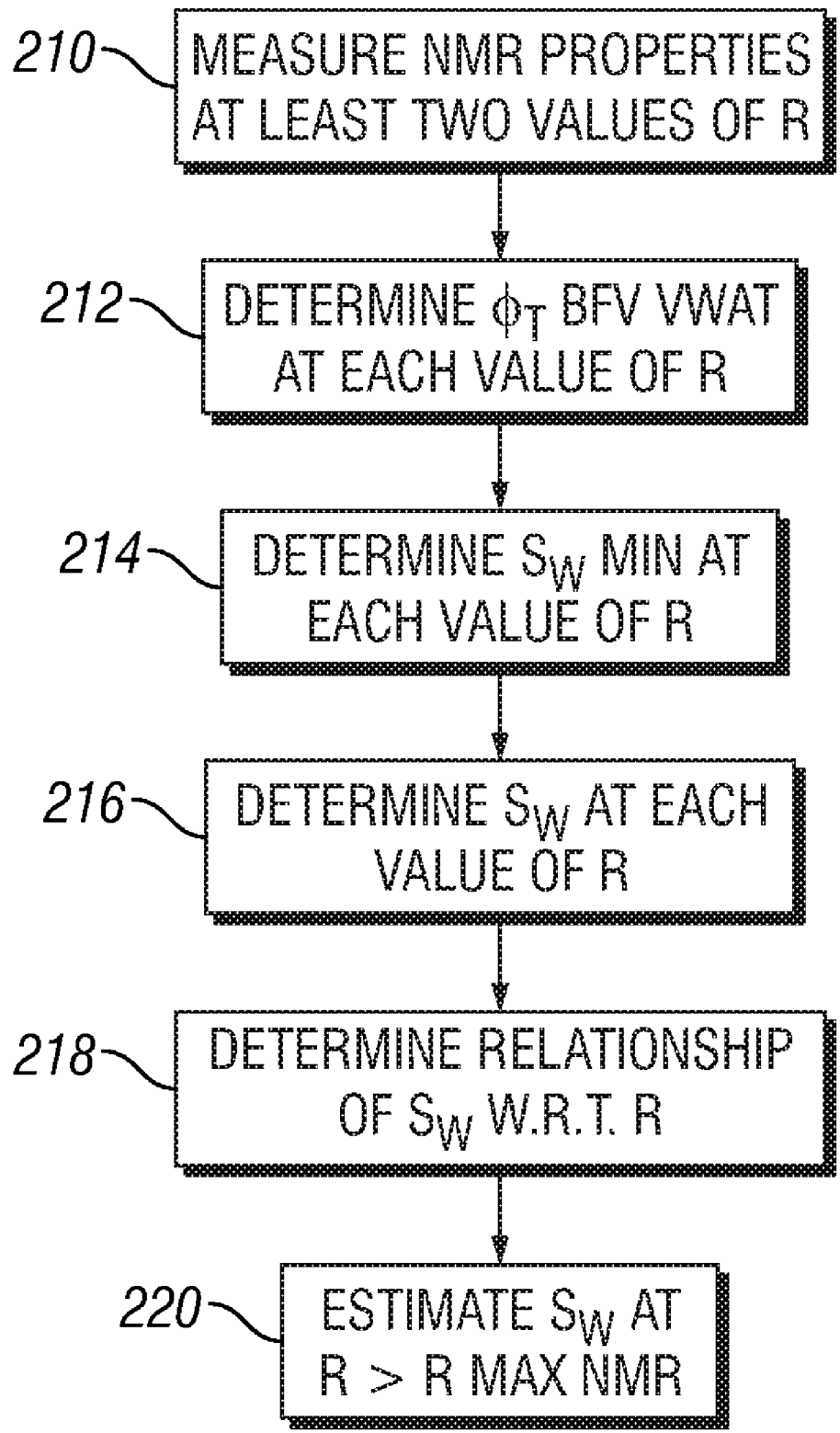
FIG. 2 shows a flow chart of one example of a method according to the invention.

In one example, NMR measurements may be made using an instrument identified by the trademark MR SCANNER, which is a trademark of the assignee the present invention. The NMR instrument, irrespective of type, is generally moved longitudinally along the wellbore and a record with respect to depth in the wellbore is made of the NMR properties of the various formations. The foregoing identified MR SCANNER instrument, in particular, can make measurements of NMR properties of the formations at a plurality of different, defined lateral depths of investigation. The lateral depths of investigation for the foregoing instrument are about 1.5 inches (3.8 cm), 2.7 inches (6.9 cm) and 4 inches (10.2 cm) from the wall of the wellbore. Referring to FIG. 2, the foregoing measurements are shown at 210. As explained above, the lateral depth of investigation of any particular NMR measurement is defined by the spatial distribution of the amplitude of the static magnetic field and the frequency of the RF magnetic field used to excite NMR phenomena. The example instrument herein is not a limitation on the scope of this invention but is provided only to illustrate the principle of the invention.

The estimated Sw at the selected lateral distance may be stored in the computer of the recording unit (22 in FIGS. 1A and 1B) for later interpretation and processing, or may be displayed on a computer display in the recording unit.

In one example, at each axial position along the wellbore for which analysis is desired, and as shown at 212 in FIG. 2, values of total porosity (represented by Phit), bound water volume (represented by BFV) and free water volume (represented by Vwat) can be determined at each lateral depth of investigation using the NMR instrument measurements corresponding to each such lateral depth. The term "axial position" along the wellbore is more commonly known as "depth" in the wellbore, however for purposes of avoiding confusion herein with the "lateral depth of investigation", reference to such depth in the wellbore will be referred to as "axial position."

In the following description other formation parameters may be denoted as follows: "Vgas" represents fractional volume of the total rock volume occupied by gas; "Voil" represents the fractional volume of the total rock volume occupied by oil; "Vobm" represents the factional volume of the total rock volume occupied by mud filtrate when oil based drilling mud is used; and "Vwat" represents the "free" water volume (which is the fractional volume of the total rock volume occupied by water that is not chemically or otherwise immobilized). The total fractional volume of pore space in the rock volume (total porosity–Phit) is related to the other of the foregoing parameters as shown in the following expression:

$$Phit = Vgas + Voil + Vobm + Vwat + BFV \quad (1)$$

The minimum amount of the fractional volume of pore space occupied by water ($Sw_{min}$ or minimum "water saturation") is related to the BFV (the volume of fluid that is immobilized, called "bound fluid"), Vwat and Phit as follows:

$$Sw_{min} = (BFV + Vwat)/Phit \quad (2)$$

See 214 in FIG. 2. The maximum water waturation ($Sw_{max}$) can be related to the foregoing and to the oil based filtrate volume by the expression:

$$Sw_{max} = (BFV + Vwat + Vobm)/Phit \quad (3)$$

As used herein the term "saturation" is intended to represent that fraction of the total amount of the pore space volume in the formation that is occupied by the fluid whose saturation is referenced. A value resulting from using the method in the present example, as shown at 216 in FIG. 2, is an estimate of the water saturation (Sw), at a selected depth of investigation r that is greater than the greatest depth of investigation of the NMR measurements. Such estimate can be made from the minimum water saturation determined from the NMR measurements made at each of the radial depths of the NMR well logging instrument (1.5 in., 2.7 in. and 4 in. in the present example) constrained by a minimum possible water saturation known as the irreducible water saturation ($Sw_{irr}$), and a maximum possible water saturation of unity (1-or 100 percent), and where it is assumed that the water saturation is monotonically increasing, monotonically decreasing or is constant with respect to the depth of investigation r. As is known in the art, the remainder of the pore space volume not determined to be occupied by water is assumed to be filled with oil, gas or mixtures thereof. Hydrocarbon saturation Sh is thus defined as (1−Sw).

The value of $Sw_{irr}$ is generally related to the ratio of BVF with respect to the total porosity. Such monotonic variation of the water saturation with respect to depth of investigation is described in Heaton et al., *Applications of the Radial Dimension in Magnetic Resonance Logging—4D NMR*, SPWLA annual symposium, Austin, Tex. (2007). The relationship of water saturation with respect to depth of investigation may be represented as a linear combination according to the following expression:

$$S(r)=a(1)K_R(1,r)+a(2)K_R(2,r) \quad (4)$$

wherein $K_R(1,r)$ is a monotonically decreasing function of r and $K_R(2,r)$ is a monotonically increasing function of r. One example of such functions can be described by trigonometric expressions:

$$K_R(1,r) = \cos^2 \frac{\pi}{2}\left(\frac{r-r_0}{r_\infty - r_0}\right) \quad (5)$$

$$K_R(2,r) = \sin^2 \frac{\pi}{2}\left(\frac{r-r_0}{r_\infty - r_0}\right)$$

in which $r_\infty$ and $r_0$ represent, respectively, the furthest lateral extent of infiltration of the mud filtrate (shown at $d_i$ in FIG. 1A), and the shallowest lateral depth in the formations at which connate (native) fluids are observable in the NMR measurements. In practice, the foregoing lateral depth values $r_\infty$ and $r_0$ are difficult to determine. However, the NMR instrument example described herein provides measurements at a plurality of defined depths of investigation that can be used as reference points for a solution to equation (4). It is also possible use a linear function to represent the relationship of water saturation with respect to lateral depth of investigation, in which case equations (4) and (5) reduce to the following:

$$S(r)=a(1)+a(2)r. \quad (6)$$

At each axial position along the wellbore for which analysis is desired, and as shown at 218 in FIG. 2, in one example of a method according to the invention the next action is to find the vector of coefficients a (with 2 components a(1), and a(2)) that minimizes the following expression:

$$\min_a \frac{1}{2}\sum_{j=1}^{3}(\hat{S}w(a,r)-Sw,j)^2 \quad (7)$$

where Sw,j represent the value of $Sw_{min}$ from the NMR measurements at the j-th depth of investigation, and the estimated $\hat{S}w(a,r)$ can be in the form of the function shown in equation (4).

The next action in the present example method, as shown at 220 in FIG. 1, is to estimate $Sw(\alpha,r)$ at a selected value of depth of investigation r. A reconstructed $Sw(\alpha,r)$ at r values equal to the particular depths of investigation provided by the NMR instrument (in the present example 1.5 in., 2.7 in. and 4 in.) can also be calculated and compared with the input values of Sw,j for quality control of the results.

The form of the estimated Sw(a,r) can also take any other form provided that the function is monotonic, such as a simple linear equation, error function or hyperpolic tangent, etc.

A method according to the invention pay provide an estimate of water saturation in formations at lateral depths from the wall of a wellbore that are greater than the depth of investigation of a nuclear magnetic resonance measuring instrument. Such methods may provide better estimation of hydrocarbons in place in a subsurface reservoir where methods for determination of hydrocarbon in place based on electrical resistivity of the formations are less reliable.

The methodology disclosed herein is not limited to the embodiments disclosed, but is also applicable to near-wellbore logging tools that estimate radial estimates of Sw, such as those associated with acoustic, dielectric or nuclear, and the like.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for estimating fluid saturation in a formation penetrated by a wellbore from nuclear magnetic resonance measurements made at a plurality of lateral depths into the formation from the wellbore, the method comprising:
    estimating a bound water volume, a total porosity and a free water volume at each of the lateral depths from the nuclear magnetic resonance measurements;
    estimating a minimum water saturation at each lateral depth from the total porosity, the free water volume and the bound water volume at each lateral depth;
    estimating a value of water saturation at each lateral depth from the minimum water saturation at each lateral depth;
    determining a relationship between lateral depth and water saturation;
    estimating water saturation at a selected lateral depth greater than the greatest lateral depth of the nuclear magnetic resonance measurements; and
    at least one of storing and displaying the estimated water saturation at the selected lateral depth.

2. The method of claim 1 further comprising determining a hydrocarbon saturation at the selected lateral depth from the estimated water saturation at the selected lateral depth.

3. The method of claim 1 wherein the nuclear magnetic resonance measurements comprise measurements of relaxation time distribution and diffusion constant.

4. The method of claim 1 wherein the relationship between lateral depth and water saturation comprises a combination of monotonically increasing saturation with respect to lateral depth and monotonically decreasing saturation with respect to lateral depth.

5. A method for well logging, comprising:
    moving a nuclear magnetic resonance instrument along a wellbore drilled through subsurface rock formations;
    measuring nuclear magnetic resonance properties at a plurality of lateral depths into the formations from a wall of the wellbore;
    corresponding to at least one axial position along the wellbore, estimating a bound water volume, a total porosity and a free water volume at each of the lateral depths from the nuclear magnetic resonance measurements;
    estimating a minimum water saturation at each lateral depth from the total porosity, the free water volume and the bound water volume at each lateral depth;
    estimating a value of water saturation at each lateral depth from the minimum water saturation at each lateral depth;
    determining a relationship between lateral depth and water saturation;
    estimating water saturation at a selected lateral depth greater than the greatest lateral depth of the nuclear magnetic resonance measurements; and
    at least one of storing and displaying the estimated water saturation at the selected lateral depth.

6. The method of claim 5 further comprising determining a hydrocarbon saturation at the selected lateral depth from the estimated water saturation at the selected lateral depth.

7. The method of claim 5 wherein the nuclear magnetic resonance measurements comprise measurements of relaxation time distribution and diffusion constant.

8. The method of claim 5 wherein the relationship between lateral depth and water saturation comprises a combination of monotonically increasing saturation with respect to lateral depth and monotonically decreasing saturation with respect to lateral depth.

9. The method of claim 5 wherein the moving the instrument comprises at least one of extending an armored electrical cable into the wellbore and withdrawing the cable from the wellbore.

10. The method of claim 5 wherein the moving the instrument comprises moving a drill string along the wellbore.

* * * * *